United States Patent [19]

Baxter et al.

[11] Patent Number: 4,675,297
[45] Date of Patent: Jun. 23, 1987

[54] GENES ENCODING BOVINE PROLACTIN

[75] Inventors: John D. Baxter; Walter L. Miller, both of San Francisco, Calif.; Joseph A. Martial, Rotheux, Belgium

[73] Assignee: The Regents of the University of California, Berkeley, Calif.

[21] Appl. No.: 532,107

[22] Filed: Sep. 14, 1983

Related U.S. Application Data

[63] Continuation of Ser. No. 236,905, Feb. 23, 1981, abandoned.

[51] Int. Cl.$^4$ .................. C12N 1/20; C12N 15/00; C12N 1/00; C12P 21/00; C12P 21/02; C12P 19/34; C07H 21/04
[52] U.S. Cl. .................. 435/253; 435/68; 435/70; 435/91; 435/172.3; 435/243; 435/317; 536/27; 935/13; 935/29; 935/72; 935/73
[58] Field of Search ............ 435/68, 70, 91, 172.3, 435/253, 317, 243; 536/27; 935/19, 21, 13, 29, 73

[56] References Cited

PUBLICATIONS

Cooke et al, "Structure of Cloned DNA Complementary to Rat Prolactin Messenger RNA", J. Biol. Chem. 255: 6502 (1980).
Villa-Komaroff et al, "A Bacterial Clone Synthesizing Proinsulin", Proc. Natl. Acad. Sci., USA 75: 3727 (1978).
Seeburg et al: "Nucleotide Sequence and Amplification in Bacteria of Structural Gene for Rat Growth Hormone", Nature 276: 7 95 (1978).
Itakura et al, "Expression in *Escherichi coli* of a Chemically Synthesized Gene for the Hormone Somatostatin", Science 198: 1056 (1977).
Martial et al, "Human Growth Hormone: Complementary DNA Cloning and Expression in Bacteria", Science 205: 602 (1979).
Chang et al, "Initiation of Protein Synthesis in Bacteria at a Translational Start Codon of Mammalian cDNA: Effects of the Preceding Nucleotide Sequence", Proc. Natl. Acad. Sci. USA 77: 1442 (1980).
Nilson et al, "Construction and Characterization of a cDNA Clone Containing a Portion of the Bovine Prolactin Sequence", Nucl. Acids Res. 8: 1561 (1980).
Miller et al, "Cloning of DNA Complementary to Bovine Prolactin mRNA", Endocrinology 107: 851 (1980).
Gubbins et al, "Construction and Analysis of Recombinant DNAs Containing a Structural Gene for Rat Prolactin", Nucl. Acids Res. 6: 915 (1979).
Brennessel et al, "Isolation and Characterization of Prolactin-Copy DNA", Biochem. Biophys. Res. Comm. 87: 635 (1979).
Nilson et al; "Ontogeny of Pituitary Hormone mRNAs in the Bovine Fetus", J. Biol. Chem. 255: 5871 (1980).
Nilson et al, "Quantitation of Fetal Pre-Prolactin mRNA in the Bovine Pituitary as a Function of Gestation", Fed. Proc. 39(6), 2017 (1980).
Nilson et al, "Purification of Pre-Prolactin mRNA from Bovine Anterior Pituitary Glands", J. Biol. Chem. 254: 1516 (1979).
Miller et al, "Molecular Cloning of Gene Sequences Coding for Bovine Growth Hormone and Prolactin", Pediatric Res. 14(4 pt. 2), 335 (1980).
Lewis, U. J., Ann Rev Physiol (1984) 46:33–42.

*Primary Examiner*—James Martinell
*Attorney, Agent, or Firm*—Ciotti & Murashige

[57] ABSTRACT

A DNA sequence encoding bovine prolactin and optionally including condons for the preceding 10 amino acids is used to construct expression systems to obtain recombinant production of these proteins.

12 Claims, No Drawings

GENES ENCODING BOVINE PROLACTIN

This is a continuation of application Ser. No. 236,905, filed Feb. 23, 1981, now abandoned.

The invention described herein was made in the course of, or under, a grant from the National Institutes of Health.

BACKGROUND OF THE INVENTION

Prolactin is a polypeptide hormone, synthesized in and secreted by the adenohypophysis (anterior lobe of the pituitary). Prolactin is synthesized as a precursor protein containing an N-terminal signal peptide and the prolactin sequence. The preliminary amino acid sequence for rat prolactin has been reported by Shome, B. and Parlow, A. F., *J.Clin.Endocrinol.Metab.*, 45, 1112 (1977). The preliminary amino acid sequence for the N-terminal signal peptide of rat prolactin has been reported by McKean, D. J. and Maurer, R. A., *Biochem.*, 17, 5215 (1978).

Prolactin was first described as being essential for the initiation of lactation in mammals at parturition. In some species, prolactin has been found to also promote milk secretion. In addition, prolactin also initiates secretion of milk in the hypertrophied mammary gland. It has been found that prolactin stimulates the synthesis of milk proteins, such as casein and α-lactalbumin. Furthermore, prolactin acts synergistically with estrogen to promote mammary gland proliferation. For a general review of the effects of prolactin see Bern, H. A. and Nicoll, C. S., *Recent Prog.Horm.Res.*, 24, 681 (1968).

Prolactin also exhibits an anti-gonadotropic hormone action. That is, prolactin inhibits luteinization by luteinizing hormone and inhibits ovulation induced by pregnant mare's serum. Prolactin induces the secretion of progesterone by the newly formed corpus luteum after ovulation. Progesterone itself inhibits ovulation and it has been noted that the antiovulatory action of prolactin depends on the presence of the corpus luteum. It thus appears that the antiovulatory effect of prolactin may be the result of the prolactin-induced progesterone synthesis by the corpus luteum.

In vitro, prolactin has been found to stimulate glucose uptake and lipogenesis in adipose tissue. When injected, prolactin has been found to mimic a number of actions of growth hormone. Uses of prolactin are based on its known biological activity discussed above. Since prolactin stimulates lactation, it can be administered to dairy cows to increase milk production.

Basic techniques for cloning DNA sequences are now known. For example, Seesburg, P. H., et al, *Nature*, 270, 486 (1977) describes the cloning of the rat growth hormone gene; Shine, J., et al, *Nature*, 270, 494 (1977) describes the cloning of the human chorionic somatomammotropin gene; and Derynck, R., et al, *Nature*, 285, 542 (1980) describes the cloning of the human fibroblast interferon gene.

Methods for the expression of heterologous DNA in a microorganism are now known. In principle, the heterologous DNA coding sequence is inserted in a DNA transfer vector at a point located within an expressible operon. This may result in the production of the desired protein either as such or as a hybrid protein. In the latter case, the inserted sequence must be in reading frame phase with the coding sequence of the operon, and oriented in the same direction with respect to translation. When the conditions are met, translation of the operon results in "read-through" to the inserted coding sequence such that the protein produced is a fusion protein comprising an N-terminal amino acid sequence coded by the expressible operon, followed by an amino acid sequence coded by the insert. See Polisky, B., et al, *Proc.Nat.Acad.Sci.USA*, 73, 3900 (1976); Itakura, K., et al, *Science*, 198, 1056 (1977). Several expressible operons have been employed, including those for β-galactosidase, β-lactamase and tryptophan.

Abbreviations used herein are those abbreviations commonly accepted and used by one of ordinary skill in the art. For example, these abbreviations are accepted by the *J.Biol.Chem.* without further elucidation.

SUMMARY OF THE INVENTION

The present invention discloses the cloning of a DNA coding for bovine prolactin and the expression of the cloned DNA in microorganisms.

mRNA coding for bovine prolactin is isolated from bovine pituitaries. A reverse transcript (a cDNA copy) of the mRNA is prepared and inserted into a transfer vector. The transfer vector is used to transform bacteria which express the cloned cDNA.

DETAILED DESCRIPTION OF THE INVENTION

A DNA sequence coding for bovine prolactin is obtained by using the cDNA method. The basic techniques of the cDNA method are known and can be illustrated by Seeburg, P. H., et al, supra. The cDNA is synthesized by using an RNA preparation extracted from bovine pituitaries as the template.

The RNA is isolated from bovine pituitaries using conventional techniques. Polyadenylated RNA is isolated by affinity chromatography. The integrity of the polyadenylated RNA is assessed by performing cell-free translation of the polyadenylated RNA as described by Miller, W. L. and McCarthy, B. J., *J.Biol.Chem.*, 254, 742 (1979) and Martial, J. A., et al, *Proc.Nat.Acad.Sci.USA*, 74, 1816 (1977) and analyzing the proteins produced by SDS-acrylamide gel electrophoresis as described by Laemmli, U. K., *Nature*, 227, 680 (1970).

The polyadenylated RNA is used as the template for preparing a double-stranded cDNA copy using conventional techniques. The first cDNA strand is synthesized using reverse transcriptase, an oligo-dT primer and the polyadenylated RNA as described by Miller and McCarthy, supra, and Monahan, J. J., et al, *Biochem.*, 15, 223 (1976). RNA is removed by alkali digestion and the single-stranded cDNA is used to self-prime the synthesis of the second strand by reverse transcriptase. The single-stranded hairpin loop is removed by digestion with S1 nuclease (Leong, J. A., et al, *J.Virol.*, 9, 891 (1972)) as described by Ullrich, A., et al, *Science*, 196, 1313 (1977).

The cDNA is now ready for insertion into an appropriate transfer vector using conventional techniques. For example, a synthetic nucleotide containing a recognition site for a particular restriction endonuclease can be blunt-end ligated to the cDNA. The cDNA and transfer vector are separately incubated with the restriction endonuclease and then annealed to form the transfer vector containing the cDNA. Alternatively, the cDNA can be dC-tailed using dCTP and terminal transferase as described by Roychoudhury, R., et al, *Nucl.Acids Res.*, 3, 863 (1976). The transfer vector, after digestion with a restriction endonuclease such as Pst I, can be dG-tailed using the same procedure. The dG-tailed transfer vector and dC-tailed cDNA are then annealed to form the transfer vector containing the cDNA. The transfer vector containing the cDNA is then used to transform a suitable host, such as *E. coli* χ1776, as described by Cooke, N. E., et al, *J.Biol.Chem.*, 255, 6502 (1980). Colonies are screened by conventional techniques. These may include (1) removing the cDNA by an appropriate restriction endonuclease and analyzing it by electrophoresis and hybridization (Southern, E. M., *J.Mol.*, 98, 503 (1975)), or (2) replica-plating as described by Grunstein, M. and Hogness, D. S., *Proc.-Nat.Acad.Sci.USA*, 72, 3961 (1975) and hybridizing with an appropriate probe, or (3) examining colonies directly for expression by RIA or other techniques.

DNA coding for bovine prolactin can be prepared from an insert coding for bovine prolactin and all or a part of the pre-sequence. The DNA coding for the prolactin and pre-sequence is removed by an appropriate restriction endonuclease. For example, if the cDNA is inserted in the Pst I site of the plasmid pBR322, the cDNA insert can be removed by digestion with Pst 1. The cDNA insert is then modified by removal of nucleotides on the 5' end of the sequence to yield a modified insert having a coding sequence for prolactin. This can be done by controlled digestion of the 3' end of the insert using, for example, T4 DNA polymerase or the Klenow fragment of DNA polymerase I. T4 DNA polymerase and the Klenow fragment of DNA polymerase I digest DNA in the 3'→5' direction in the absence of deoxynucleotides. If any one of the deoxynucleotides is present, digestion of the DNA strand will proceed until that base is encountered. Thus, by incubating the cDNA insert containing part of the prolactin pre-sequence with T4 DNA polymerase, for example, for a short period of time and then adding dTTP and continuing the incubation, the 3'→5' portion of the pre-sequence will be removed. The single-stranded region is then removed by digestion with S1 nuclease as described by Ullrich, A., et al, supra. Further details of this modification procedure are set forth in Example 5. After the cDNA has been modified to remove the pre-sequence, it is then inserted into an appropriate transfer vector as described above.

The cloned DNA is expressed in bacteria to yield either a fusion protein comprising the prolactin coded by the inserted sequence, or the prolactin itself. Several possible techniques are available as options, and may include (a) modification of the coding sequences to provide an exact desired translational starting point; (b) selection or construction of an optimal expression vector; (c) post-translational processing, either by exploiting in vivo processing activity of the host or by in vitro chemical means; and (d) direct expression.

When a fusion protein is expressed, modification of the cloned nucleotide sequence will generally be unnecessary as long as the resulting sequence permits translation of the insert in the correct reading frame and no stop codons intervene before the initial codon of the inserted sequence.

Prolactin (or prolactin plus ten amino acids of the pre-sequence) is expressed as a fusion protein by insertion of the cDNA into appropriate sites within expressed operons (expression vectors) including, for example, the Pst I site in the β-lactamase gene of pBR322 (Villa-Komaroff, L., et al, *Proc.Nat.Acad.Sci.USA*, 75, 3727 (1978) and Seeburg, P., et al, *Nature*, 274, 795 (1978)), the EcoRI site of pBR322 carrying the lac control region and coding sequence for β-galactosidase (Itakura, K., et al, supra) or the HindIII site of the trpD gene of plasmid ptrpED50 (Martial, J., et al, *Science*, 205, 602 (1979)). Modifications of sequence length by one or two nucleotides in order to achieve correct reading frame phase are well known in the art. Insertions at the Pst I site of pBR322, with the aid of the tailing procedure, occur in correct orientation and reading frame with a probability of 1/6.

Prolactin is prepared from a fusion protein susceptible of specific cleavage in vitro. The cloned nucleotide sequence is modified to code for amino acid sequences providing specificity for a proteolytic enzyme. A useful sequence is AspAspAspAspLys, cleaved preferentially by the enzyme enterokinase. A linking nucleotide sequence coding for the foregoing amino acid sequence is inserted adjacent the nucleotide sequence coding for the amino terminus prolactin.

Such insertion requires modification of the original cDNA insert, by removal of nucleotides on the 5' end of the pre-sequence of the prolactin coding sequence. This is accomplished as described above. The linker nucleotide sequence coding for the foregoing amino acid sequence is blunt-end ligated to the cDNA using DNA ligase as described by Valenzuela, et al, *Nature*, 280, 815 (1979). The modified cDNA sequence is inserted into a fusion protein expression vector as previously described. Host bacteria, *E. coli* HB101, RR1, χ1776 or other bacteria are transformed by the recombinant vectors bearing the inserted prolactin coding region. Transformants are screened using $^{32}P$ nick-translated bovine prolactin cDNA. Transformants are then grown under conditions suitable for expression of the fusion protein. After expression of the fusion protein, the prolactin is cleaved out by enzymatic hydrolysis using enterokinase.

By the use of appropriate expression transfer vectors, the prolactin of the present invention is expressed directly, i.e., not fused to any procaryotic protein. Chang, A. C. Y., et al, *Proc.Nat.Acad.Sci.USA*, 77, 1442 (1980) have reported that they obtained direct expression of mouse dihydrofolate reductase (DHFR). The mouse DHFR coding sequence had been dC-tailed and inserted into the dG-tailed, Pst I site of pBR322. The authors found that transformed bacteria synthesized a protein having enzymatic properties, immunological reactivity and molecular size of the mouse DHFR. They also found that the cDNA for DHFR was in a different translation reading frame from the bacterial β-lactamase gene into which it had been inserted. These findings implied that translation was reinitiated at the start codon for the mouse DHFR under these circumstances, i.e., method of insertion, to produce mouse DHFR directly and not as part of a fusion protein.

The underlying principle of another form of direct expression is that the inserted DNA segment entirely replaces the coding segment normally transcribed and translated by the bacterial control region. The essential component of the control region to be preserved is termed the expression unit, which includes a promoter and a ribosomal binding site capable of acting in the host organism. It is not necessary to remove all of the nucleotides coding for the host portion of the fusion protein. The relationship between the ribosomal binding site and the start codon (AUG) is such that the start codon may be located anywhere within 3–11 nucleotides of the ribosomal binding site. Shine, J., et al, *Proc.-Nat.Acad.Sci.USA*, 71, 1342 (1974) and Steitz, J., et al,

*Proc.Nat.Acad.Sci. USA,* 72, 4734 (1975). In this 3-11 nucleotide region, the first AUG to be encountered sets the reading frame for translation. In the case of ptrpE30, derived from ptrpED50 described, supra, and containing the operator, promoter, leader, attenuator and ribosome binding sequences of the tryptophan operon together with the nucleotide sequence coding for seven amino acids of the trpE protein followed by a HindIII site, the removal of a minimum of 23-29 nucleotides from the HindIII site provides a site for insertion of the cDNA insert under tryptophan operon control.

A vector for direct expression can be constructed by modification of ptrpE30 by removing 23-29 nucleotides using T4 DNA polymerase and S1 nuclease as described above. A linker nucleotide sequence containing the restriction sequence for BamHI endonuclease and the start codon (ATG) is blunt-end ligated to the prolactin cDNA and a BamHI linker is ligated to the modified ptrpE30 by the procedure of Valenzuela, et al, supra. This is done to facilitate insertion which is performed essentially as described by Ullrich, A., et al, supra. Host bacteria *E. coli* HB101, RR1, χ1776 or other bacteria are transformed by the recombinant vectors bearing the inserted prolactin coding region. Transformants are screened as described above and then grown under conditions suitable for expression of prolactin. Prolactin can also be expressed directly by following the procedure described in Goeddel, D. V., et al, *Nature,* 281, 544 (1979).

Alternatively, bovine prolactin can be expressed directly utilizing the expression vector, ptrpL1, described in Example 6 and the relevant portions being set forth at the end of the examples herein. Hallewell, R. A. and Emtage, S., *Gene* 9:27-47 (1980) describe the preparation of an expression vector, ptrpED5-1, containing the promoter, operator, leader, attenuator, trp E gene and 15% of the trp D gene sequences. This vector contains the promoter, operator and leader ribosomal binding site of the trp operon. A ClaI restriction site exists near the ribosomal binding site. Preferably, a linker coding for methionine - ClaI site - methionine (Met-Cla-Met) is blunt-end ligated to the cDNA coding for prolactin.

The modified cDNA and ptrpL1 are cleaved by ClaI, ligated together, used to transform bacteria and screened as described above. The selected colonies are then grown under conditions suitable for expression of prolactin. Bovine prolactin synthesized as described is purified by techniques well known in the art, including, for example, gel filtration, ion exchange chromatography, affinity chromatography and differential solubility techniques.

The details of the present invention will be further described by the following examples. In these examples, digestions with restriction endonuclease were carried out under conditions optimized for each enzyme. Restriction endonucleases, their nomenclature and site specificity have been described in detail by Roberts, R., *Nucl.Acids Res.,* 8, r63 (1980). Enzymes were obtained commercially (New England Biolabs, Cambridge, MA, Bethesda Research Labs, Bethesda, MD, and Boehringer-Mannheim, Indianapolis, IN) and optimal conditions according to supplier's recommendations were employed unless noted otherwise. Reverse transcriptase was provided by Dr. J. Beard, Life Sciences, Inc., St. Petersburg, FL. The use of reverse transcriptase and suitable reaction conditions have been described previously by Seeburg, P. H., et al, *Nature,* 276, 795 (1978); Seeburg, P. H., et al, supra; and Shine, J., et al, supra. T4 DNA polymerase was obtained from New England BioLabs. The use of T4 DNA polymerase is described in Example 5. Micrococcal S1 nuclease was obtained from Miles Laboratories, Elkhart, IN. The use of S1 nuclease and suitable reaction conditions have been previously described by Ullrich, A., supra. Terminal deoxynucleotide transferase was obtained from Enzo Biochemicals, New York, NY. The use of this enzyme and suitable reaction conditions have been previously described by Roychoudhury, et al, supra. The Klenow fragment of DNA polymerase I was obtained from Boehringer Biochemicals, Indianapolis, IN.

EXAMPLE 1

Synthesis of bovine prolactin cDNA

Female bovine pituitaries were collected shortly after killing and were frozen immediately in liquid nitrogen. Total RNA was prepared by homogenizing the pituitaries in a guanidine thiocyanate solution (Chirgwin, J. M., et al, *Biochem.,* 18, 5294 (1979)). The RNA was centrifuged through 5.7M CsCl as described by Ullrich, A., et al, supra. The RNA was then extracted with phenol and precipitated with ethanol. Polyadenylated RNA was purified using oligo-dT-cellulose affinity chromatography as described by Miller and McCarthy, supra, and Aviv, H. and Leder, P., *Proc.Nat.Acad.Sci. USA,* 69, 1408 (1972).

The polyadenylated RNA was translated in a cell-free system using rabbit reticulocytes as described by Miller and McCarthy, supra, and Martial, J. A., et al, supra, (1977). Bovine prolactin synthesized in this system was immune-precipitated using a heterologous anti-ovine prolactin antiserum and prepared by adsorption to formalin-fixed *Staphylococcus aureus* Cowan strain I as described by Martial, J. A., et al, supra, (1977). The $^{35}$S-proteins were electrophoresed on 12.5% SDS slab polyacrylamide gels as described by Laemmli, supra. This analysis indicated that polyadenylated RNA coding for bovine prolactin represented about 18.0% of the total pituitary polyadenylated RNA.

Polyadenylated RNA was reverse-transcribed into single-stranded cDNA using reverse transcriptase by the procedure described by Miller and McCarthy, supra, and Monahan, et al, supra. RNA was removed by alkaline hydrolysis. The single-stranded cDNA was extracted with phenol, chromatographed over G-50 Sephadex (trademark, Pharmacis, Inc., Uppsala, Sweden) and ethanol-precipitated. The single-stranded cDNA was used to self-prime the synthesis of the second strand of cDNA using reverse transcriptase as described above. The single-stranded "hairpin loop" at the 3' end of the first strand of cDNA was removed by digestion with S1 nuclease as described by Leong et al, supra, and Ullrich, A., et al, supra. The double-stranded cDNA was purified by phenol extraction, chromatography over G-50 Sephadex and ethanol precipitation. The double-stranded cDNA was 3'dCMP-tailed using dCTP and terminal transferase as described by Roychoudhury et al, supra.

Plasmid pBR322 was cleaved by Pst I endonuclease and tailed with dGMP by the previously described tailing procedure except that dGTP is used instead of dCTP. 50 ng of the dG-tailed, Pst I-cleaved plasmid pBR322 and 20 ng of the dC-tailed double-stranded cDNA were annealed in a 50 μl reaction as described by Cooke, et al, supra.

Transformation of E. coli χ1776 with the plasmid preparation was carried out as follows. E. coli χ1776 were rendered permeable to DNA by incubation in 75 mM CaCl₂, 5 mM MgCl₂, 10 mM Tris, pH 7.5, for 20 minutes at 4° C. Plasmid and bacteria were incubated for 60 minutes at 4° C., and then two minutes at 41° C. Transformed colonies were selected for tetracycline resistance. Plasmid DNA was prepared from several colonies, cut with Pst I, electrophoresed on 1% agarose, stained with ethidium bromide and photographed and finally transferred to nitrocellulose filters by the method of Southern, supra, as described by Miller, W. L., et al, *Endocrinology*, 107, 851 (1980). In the Miller et al., procedure, filter-bound DNA was hybridized with ³²P-labeled bovine pituitary cDNA, so as to identify which colonies contained cloned cDNA. Filters washed clean of hybridized cDNA were hybridized with previously cloned rat prolactin cDNA also labeled with ³²P. One plasmid which was found to hybridize to rat prolactin cDNA was identified by Miller et al. as pBP261. Miller, et al analyzed this plasmid and determined that it contained 378 base pairs and the nucleotide sequence coding for amino acids 99–199 of bovine prolactin.

This DNA was then used as a probe for isolating a plasmid containing the entire sequence of bovine prolactin. Bovine prolactin cDNA was isolated from pBP261 and labelled to high specific activity by nick-translation with ³²P, as described by Maniatis, R., et al, *Proc. Nat. Acad. Sci. USA*, 72, 1184 (1975). The colonies which had hybridized to labelled pituitary cDNA were cleaved with Pst I and analyzed by agarose gel and Southern hybridization (Southern, supra) using this probe. Nine colonies were found to contain bovine prolactin cDNA. Plasmid DNA was prepared from these colonies, cut with Pst I and displayed on a polyacrylamide gel. The largest insert—having 702 base pairs—was selected for further analysis. The plasmid was designated pBP292.

EXAMPLE 2

Sequence analysis of the cDNA

Plasmid pBP292 was cut with Pst I and the phosphate on the 5' ends of the DNA fragments was removed with alkaline phosphatase and replaced with [³²P] phosphate using polynucleotide kinase. Subsequent cutting with a variety of other restriction endonucleases, polyacrylamide gel electrophoresis, and staining and autoradiography of the bands of DNA provide a restriction map of the cloned DNA. A large batch of pBP292 was then prepared and cut with Pst I, Pvu II or Taq I, labelled with [γ³²P] ATP and polynucleotide kinase, and then cut with other enzymes to yield DNA fragments labelled at a single end. These fragments were prepared for elution from polyacrylamide gel and sequenced as described by Cooke et al, supra, and Maxam, A. M. and Gilbert, W., *Proc. Nat. Acad. Sci. USA*, 74, 1560 (1977). The sequence for the inserted cDNA is shown in Table 1, together with the corresponding predicted amino acid sequence coded by the sense strand, i.e., the strand corresponding in sequence to the respective mRNA.

The correct reading frame is recognized by the lack of termination codons over a substantial portion of the inserts. The amino acid positions are numbered beginning with the amino-terminal amino acid of bovine prolactin and proceeding in the positive direction to the carboxy terminal end and in the negative direction for a portion of the presumed pre-sequence. The sequence suggests, in common with many other hormones, the synthesis of growth hormone involves post-translational processing. The translation of prolactin mRNA yields a precursor, preprolactin, containing a signal peptide which may be released during the transit into the endoplasmic reticulum.

TABLE 1

| −10 | | | | | | | | | | | | | 1 |
|---|---|---|---|---|---|---|---|---|---|---|---|---|---|
| asn | leu | leu | leu | cys | gln | gly | val | val | ser | thr | pro | val | cys | pro |
| AAT | CTA | CTC | TTG | TGC | CAG | GGT | GTG | GTC | TCC | ACC | CCC | GTC | TGT | CCC |

| | | | | 10 | | | | | | | | | | 20 |
|---|---|---|---|---|---|---|---|---|---|---|---|---|---|---|
| asn | gly | pro | gly | asn | arg | gln | val | ser | leu | arg | asp | leu | phe | asp |
| AAT | GGG | CCT | GGC | AAC | CGC | CAG | GTA | TCC | CTT | CGA | GAC | CTG | TTT | GAC |

| | | | | | | | | 30 | | | | | | |
|---|---|---|---|---|---|---|---|---|---|---|---|---|---|---|
| arg | ala | val | met | val | ser | his | tyr | ile | his | asp | leu | ser | ser | glu |
| CGG | GCA | GTC | ATG | GTG | TCC | CAC | TAC | ATC | CAT | GAC | CTC | TCC | TCG | GAA |

| | | | | 40 | | | | | | | | | | 50 |
|---|---|---|---|---|---|---|---|---|---|---|---|---|---|---|
| met | phe | asn | glu | phe | asp | lys | arg | tyr | ala | gln | gly | lys | gly | phe |
| ATG | TTC | AAC | GAA | TTT | CAT | AAA | CGG | TAT | GCC | CAG | GGC | AAA | GGG | TTC |

| | | | | | | | | 60 | | | | | | |
|---|---|---|---|---|---|---|---|---|---|---|---|---|---|---|
| ile | thr | met | ala | leu | asn | ser | cys | his | thr | ser | ser | leu | pro | thr |
| ATT | ACC | ATG | GCC | CTC | AAC | AGC | TGC | CAT | ACC | TCC | TCC | CTT | CCT | ACC |

| | | | | 70 | | | | | | | | | | 80 |
|---|---|---|---|---|---|---|---|---|---|---|---|---|---|---|
| pro | glu | asp | lys | glu | gln | ala | gln | gln | thr | his | his | glu | val | val |
| CCT | GAA | GAT | AAA | GAA | CAA | GCC | CAA | CAG | ACC | CAC | CAT | GAA | GTC | GTT |

| | | | | | | | | 90 | | | | | | |
|---|---|---|---|---|---|---|---|---|---|---|---|---|---|---|
| met | ser | leu | ile | leu | gly | leu | leu | arg | ser | trp | asn | asp | pro | leu |
| ATG | AGC | TTG | ATT | CTT | GGG | TTG | CTG | CGC | TCC | TGG | AAT | GAC | CCT | CTG |

| | | | | 100 | | | | | | | | | | 110 |
|---|---|---|---|---|---|---|---|---|---|---|---|---|---|---|
| tyr | his | leu | val | thr | glu | val | arg | gly | met | lys | gly | ala | pro | asp |
| TAT | CAC | CTA | GTC | ACC | GAG | GTA | CGG | GGT | ATG | AAA | GGA | GCC | CCA | GAT |

| | | | | | | | | 120 | | | | | | |
|---|---|---|---|---|---|---|---|---|---|---|---|---|---|---|
| ala | ile | leu | ser | arg | ala | ile | glu | ile | glu | glu | glu | asn | lys | arg |
| GCT | ATC | CTA | TCG | AGG | GCC | ATA | GAG | ATT | GAG | GAA | GAA | AAC | AAA | CGA |

TABLE 1-continued

| | | | | 130 | | | | | | | | | | 140 |
|---|---|---|---|---|---|---|---|---|---|---|---|---|---|---|
| leu | leu | glu | gly | met | glu | met | ile | phe | gly | gln | val | ile | pro | gly |
| CTT | CTG | GAA | GGC | ATG | GAG | ATG | ATA | TTT | GGC | CAG | GTT | ATT | CCT | GGA |
| | | | | | | | | 150 | | | | | | |
| ala | lys | glu | thr | glu | pro | tyr | pro | val | trp | ser | gly | leu | pro | ser |
| GCC | AAA | GAG | ACT | GAG | CCC | TAC | CCT | GTG | TGG | TCA | GGA | CTC | CCG | TCC |
| | | | | 160 | | | | | | | | | | 170 |
| leu | gln | thr | lys | asp | glu | asp | ala | arg | tyr | ser | ala | phe | tyr | asn |
| CTG | CAA | ACT | AAG | GAT | GAA | GAT | GCA | CGT | TAT | TCC | GCT | TTT | TAT | AAC |
| | | | | | | | | | 180 | | | | | |
| leu | leu | his | cys | leu | arg | arg | asp | ser | ser | lys | ile | asp | thr | tyr |
| CTG | CTC | CAC | TGC | CTG | CGC | AGG | GAT | TCA | AGC | AAG | ATT | GAC | ACT | TAC |
| | | | | 190 | | | | | | | | | 199 | |
| leu | lys | leu | leu | asn | cys | arg | ile | ile | tyr | asn | asn | asn | cys | OC |
| CTT | AAG | CTC | CTG | AAT | TGC | AGA | ATC | ATC | TAC | AAC | AAC | AAC | TGC | TAA |

GCCCACATTGTACCTTTCCATTTCTGAGATGGTTCTTAATGATCCATTCCCTGGCAA

ACTTCTCTGAGCTTT

EXAMPLE 3

Synthesis of cDNA coding for bovine prolactin

Plasmid pBP292 is digested with Pst I removing the 702 base pair insert which is purified by preparative gel electrophoresis. A 15 μg sample of purified insert DNA is then modified by suspending the DNA in water to which is added a concentrated solution of salts such that the final composition comprises 70 mM Tris, pH 8.8, 70 mM MgCl$_2$, 10 mM dithiothreitol and 13.75 units of T4 DNA polymerase in a total volume of 250 μl. The reaction mixture is briefly incubated at 37° C. and then an excess of dTTP is added and incubation continued for several minutes. The enzyme is inactivated by heat treatment at 65° C. for five minutes. The treated DNA is recovered by ethanol precipitation. Digestion with S1 nuclease to provide blunt ends is carried out as described by Ullrich, A., et al, supra. The products are then electrophoresed on polyacrylamide gels. A DNA having approximately 672 base pairs is selected, cloned and screened as described in Example 1. One plasmid is isolated and analyzed as described in Example 2. The cDNA insert has the nucleotide sequence illustrated in Table 1 beginning with the ACC codon at position 1.

EXAMPLE 4

Expression of bovine prolactin

Bovine prolactin can be expressed by any of the methods described above. For purposes of illustration only, production of bovine prolactin by direct expression will be described.

A vector for direct expression is constructed by modification of the plasmid ptrpE30, by removal of 23-29 nucleotides using T4 DNA polymerase and S1 nuclease essentially as described in Example 3. Plasmid ptrpE30 is first cut with HindIII and then incubated with T4 DNA polymerase. The reaction is stopped by the addition of any one deoxynucleotide and the enzyme is inactivated. The single-stranded DNA is then removed by digestion with S1 nuclease. The modified plasmid is purified by gel electrophoresis. The modified expression vector is provided with a specific linker having the sequence 5'-CCGGATCCGG-3' on one strand and its complementary sequence on the other by blunt-end ligation using DNA ligase as described by Valenzuela, supra. A specific linker having the sequence 5'-CCGGATCCGGATG-3' on one strand and its complementary sequence on the other strand is blunt-end ligated to the bovine prolactin cDNA prepared as described in Example 3. The linkers provide restriction sites sensitive to BamHI endonuclease which are employed to facilitate insertion. Insertion is accomplished by following the procedure of Ullrich, A., et al, supra. Host bacteria E. coli HB101 or E. coli χ1776 are transformed by the recombinant vectors bearing the inserted prolactin coding region and transformants are screened as described in Example 1. A single transformant designated ptrpE30/bPr1 is selected for further analysis.

Bacterial cells transformed by ptrpE30/bPr1 are grown in a standard minimal medium (M9) supplemented with Leu, Pro, vitamin B1 and ampicillin at 37° C. In early log phase, the trp operon is induced by the addition of β-indolylacrylic acid (30 μg/ml medium). Control cultures are left uninduced. After three more hours of growth, 1.5 ml of cells are radioactively labelled by the addition of 20 μCi of $^{35}$S-L-Met and incubated for 10 minutes. The cells are collected by centrifugation, washed and resuspended in 250 μl of buffer containing 10% (v/v) glycol, 5% (v/v) β-mercaptoethanol and 2.3% (w/v) SDS in 0.0625 M Tris, pH 6.8. The suspension is boiled for five minutes, then applied to a 10° (w/v) SDS-polyacrylamide gel and fractionated by electrophoresis. The protein bands are visualized by autoradiography. The results show the existence of a new protein band of about 26,000 daltons not observed in the uninduced or non-transformed cultures.

The bovine prolactin is purified by conventional techniques including, for example, gel filtration, ion exchange chromatography, affinity chromatography and differential solubility techniques.

EXAMPLE 5

This example describes modification of a polynucleotide chain to sequentially remove terminal nucleotides. A specific purification linker is provided by modifying a linker having the sequence 5'-GATGATGAT-GATAAA-3'. The sequence is modified at the 3'-end by providing a C or preferably a T residue in place of the G. The modification can be accomplished by the use of T4 DNA polymerase in the presence of ATP and CTP to remove the 3'-terminal G, followed by S₁ nuclease to remove the 5'-terminal C on the complementary strand. A C or preferably a T may be added to the 3'-end, either by enzymatic or chemical means. The resulting sequence codes for the amino acids AspAspAspAspAsn. Similarly, a modified insert for bovine prolactin can be prepared from a DNA insert coding for bovine prolactin and all or part of the pre-sequence.

EXAMPLE 6

10 μg of ptrpED5-1 was digested with HinfI and the resulting fragments made flush-ended by a 10 minute incubation at 20° C. with the Klenow fragment of DNA polymerase I in a reaction volume of 20 μl containing 1 μl of the polymerase, 50 mM Tris pH 7.5, 10 mM MgCl₂, 500 μM each of dATP, dTTP, dCTP and dGTP and 10 mM 2-mercaptoethanol. The 500 base pair HinfI fragment containing the trp regulatory region was eluted from a 5% acrylamide gel and ethanol precipitated. The HinfI fragment was then ligated to a hundred-fold molar excess of synthetic HindIII linker molecules (d(pCCAAGCTTGG)) in a reaction volume of 30 μl containing 2 μl T4 DNA ligase, 50 mM Tris pH 7.5, 10 mM MgCl₂, 10 mM dithiothreitol and 1 mM rATP at 15° C. for 16 hours. The ligase is inactivated by heat treatment at 68° C. for 5 minutes. The HindIII linker treated HinfI fragment was cut with HindIII, the mixture was extracted with phenol-chloroform and ethanol precipitated. Excess linker molecules and linker molecule fragments were removed from the HinfI fragment by chromatography on Sepharose ™ CL 4B (Pharmacia, Inc., Uppsala, Sweden). The plasmid pBR322 was cut with HindIII, treated with alkaline phosphatase and the HinfI fragment inserted into the HindIII site by following the procedure described by Ullrich et al, supra. Host bacteria *E. coli* RRI were transformed by the resulting recombinant vector bearing the 500 base pair Hinf fragment and transformants were selected for resistance to ampicillin. A recombinant clone with the trp promoter directed towards the β-lactamase gene was obtained by screening DNA miniscreens for a 200 base pair HpaI-EcoRI fragment. This plasmid was designated ptrpE2-1.

A first portion of the plasmid ptrpE2-1 was digested with a mixture of HpaI and TaqI and a 34 base pair HpaI-TaqI fragment was purified by polyacrylamide gel electrophoresis. A second portion of the plasmid ptrpE2-1 was digested with a mixture of ClaI and HpaI. The ClaI-HpaI treated ptrpE2-1, i.e. ptrpE2-1 lacking a ClaI-HpaI fragment, was purified by polyacrylamide gel electrophoresis and then ligated to a three-fold molar excess of the purified HpaI-TaqI fragment using T4 DNA ligase following the procedure described by Ullrich et al, supra. Host bacteria *E. coli* HB101 were transformed by the resulting recombinant vector bearing the promoter, operator and leader ribosomal binding site of the trp operon. Transformants were selected for resistance to ampicillin. A recombinant clone was obtained by screening DNA miniscreens for a 34 base pair HpaI-ClaI fragment. This plasmid was designated ptrpL1. The plasmid was also found to contain a single ClaI site, a single HindIII site and the expected DNA sequence around the ClaI site.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

What is claimed is:

1. A DNA which comprises a recombinant DNA sequence encoding a bovine prolactin of the amino acid sequence

```
1                                       10
thr pro val cys pro asn gly pro gly asn arg
ACC CCC GTC TGT CCC AAT GGG CCT GGC AAC CGC 20
gln val ser leu arg asp leu phe asp arg ala
CAG GTA TCC CTT CGA GAC CTG TTT GAC CGG GCA 30
val met val ser his tyr ile his asp leu ser
GTC ATG GTG TCC CAC TAC ATC CAT GAC CTC TCC 40
ser glu met phe asn glu phe asp lys arg tyr
TCG GAA ATG TTC AAC GAA TTT GAT AAA CGG TAT 50
ala gln gly lys gly phe ile thr met ala leu
GCC CAG GGC AAA GGG TTC ATT ACC ATG GCC CTC 60
asn ser cys his thr ser ser leu pro thr pro
AAC AGC TGC CAT ACC TCC TCC CTT CCT ACC CCT 70
glu asp lys glu gln ala gln gln thr his his
GAA GAT AAA GAA CAA GCC CAA CAG ACC CAC CAT 80
glu val val met ser leu ile leu gly leu leu
GAA GTC GTT ATG AGC TTG ATT CTT GGG TTG CTG 90
arg ser trp asn asp pro leu tyr his leu val
CGC TCC TGG AAT GAC CCT CTG TAT CAC CTA GTC 100                                     110
thr glu val arg gly met lys gly ala pro asp
ACC GAG GTA CGG GGT ATG AAA GGA GCC CCA GAT 120
ala ile leu ser arg ala ile glu ile glu glu
GCT ATC CTA TCG AGG GCC ATA GAG ATT GAG GAA 130
glu asn lys arg leu leu glu gly met glu met
CAA AAC AAA CGA CTT CTG GAA GGC ATG GAG ATG 140
ile phe gly gln val ile pro gly ala lys glu
ATA TTT GGC CAG GTT ATT CCT GGA GCC AAA GAG 150
thr glu pro tyr pro val trp ser gly leu pro
ACT GAG CCC TAC CCT GTG TGG TCA GGA CTC CCG 160
ser leu gln thr lys asp glu asp ala arg tyr
TCC CTG CAA ACT AAG GAT GAA GAT GCA CGT TAT 170
ser ala phe tyr asn leu leu his cys leu arg
TCC GCT TTT TAT AAC CTG CTC CAC TGC CTG CGC 180
arg asp ser ser lys ile asp thr tyr leu lys
AGG GAT TCA AGC AAG ATT GAC ACT TAC CTT AAG 190
leu leu asn cys arg ile ile tyr asn asn
CTC CTG AAT TGC AGA ATC ATC TAC AAC AAC
```

199
asn cys
AAC TGC

2. The DNA of claim 1 which further comprises a deoxyribonucleotide sequence encoding the amino acid sequence

```
     -10
     asn leu leu leu cys gln gly val val ser
     AAT CTA CTC TTG TGC CAG GGT GTG GTC TCC
``` so that said DNA encodes the amino acid sequence

```
     -10                                          1
     asn leu leu leu cys gln gly val val ser thr
     AAT CTA CTC TTG TGC CAG GGT GTG GTC TCC ACC 10
     pro val cys pro asn gly pro gly asn arg gln
     CCC GTC TGT CCC AAT GGG CCT GGC AAC CGC CAG 20
     val ser leu arg asp leu phe asp arg ala val
     GTA TCC CTT CGA GAC CTG TTT GAC CGG GCA GTC 30
     met val ser his tyr ile his asp leu ser ser
     ATG GTG TCC CAC TAC ATC CAT GAC CTC TCC TCG 40
     glu met phe asn glu phe asp lys arg tyr ala
     GAA ATG TTC AAC GAA TTT GAT AAA CGG TAT GCC 50
     gln gly lys gly phe ile thr met ala leu asn
     CAG GGC AAA GGG TTC ATT ACC ATG GCC CTC AAC 60
     ser cys his thr ser ser leu pro thr pro glu
     AGC TGC CAT ACC TCC TCC CTT CCT ACC CCT GAA 70
     asp lys glu gln ala gln gln thr his his glu
     GAT AAA GAA CAA GCC CAA CAG ACC CAC CAT GAA 80
     val val met ser leu ile leu gly leu leu arg
     GTC GTT ATG AGC TTG ATT CTT GGG TTG CTG CGC 90                                       100
     ser trp asn asp pro leu tyr his leu val thr
     TCC TGG AAT GAC CCT CTG TAT CAC CTA GTC ACC
```

```
                                              110
     glu val arg gly met lys gly ala pro asp ala
     GAG GTA CGG GGT ATG AAA GGA GCC CCA GAT GCT 120
     ile leu ser arg ala ile glu ile glu glu glu
     ATC CTA TCG AGG GCC ATA GAG ATT GAG GAA GAA 130
     asn lys arg leu leu glu gly met glu met ile
     AAC AAA CGA CTT CTG GAA GGC ATG GAG ATG ATA 140
     phe gly gln val ile pro gly ala lys glu thr
     TTT GGC CAG GTT ATT CCT GGA GCC AAA GAG ACT 150
     glu pro tyr pro val trp ser gly leu pro ser
     GAG CCC TAC CCT GTG TGG TCA GGA CTC CCG TCC 160
     leu gln thr lys asp glu asp ala arg thr ser
     CTG CAA ACT AAG GAT GAA GAT GCA CGT TAT TCC 170
     ala phe tyr asn leu leu his cys leu arg arg
     GCT TTT TAT AAC CTG CTC CAC TGC CTG CGC AGG 180
     asp ser ser lys ile asp thr tyr leu lys leu
     GAT TCA AGC AAG ATT GAC ACT TAC CTT AAG CTC 190                               199
     leu asn cys arg ile ile tyr asn asn asn cys
     CTG AAT TGC AGA ATC ATC TAC AAC AAC AAC TGC.
```

3. A DNA transfer vector which comprises the DNA of claim 1.

4. A DNA transfer vector which comprises the DNA of claim 2.

5. A microorganism transformed by the transfer vector of claim 3.

6. A microorganism transformed by the transfer vector of claim 4.

7. A DNA expression vector which comprises the DNA of claim 1.

8. A DNA expression vector which comprises the DNA of claim 2.

9. A microorganism transformed by the expression vector of claim 7.

10. A microorganism transformed by the expression vector of claim 8.

11. The microorganism of claim 5 or 6 comprising *Escherichia coli* χ1776.

12. The microorganism of claim 9 or 10 comprising *Escherichia coli* χ1776 or *Escherichia coli* HB101.

* * * * *